United States Patent
Adachi

(10) Patent No.: US 10,334,144 B2
(45) Date of Patent: Jun. 25, 2019

(54) IMAGING DEVICE, ENDOSCOPE, AND ENDOSCOPE SYSTEM

(71) Applicant: OLYMPUS CORPORATION, Tokyo (JP)

(72) Inventor: Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 23 days.

(21) Appl. No.: 15/791,613

(22) Filed: Oct. 24, 2017

(65) Prior Publication Data

US 2018/0048790 A1 Feb. 15, 2018

Related U.S. Application Data

(63) Continuation of application No. PCT/JP2016/007767, filed on Sep. 20, 2016.

(30) Foreign Application Priority Data

Oct. 20, 2015 (JP) ................. 2015-206637

(51) Int. Cl.
*H04N 5/225* (2006.01)
*A61B 1/00* (2006.01)
(Continued)

(52) U.S. Cl.
CPC ....... *H04N 5/2251* (2013.01); *A61B 1/00009* (2013.01); *A61B 1/045* (2013.01);
(Continued)

(58) Field of Classification Search
CPC ....... A61B 1/00009; A61B 1/045; A61B 1/05; G02B 23/2484; H04N 5/2253;
(Continued)

(56) References Cited

U.S. PATENT DOCUMENTS

| 5,777,508 A | 7/1998 | Sawanobori |
| 2004/0073086 A1 | 4/2004 | Abe |

(Continued)

FOREIGN PATENT DOCUMENTS

| JP | 2003052628 A | 2/2003 |
| JP | 2003153858 A | 5/2003 |

(Continued)

OTHER PUBLICATIONS

International Search Report dated Nov. 8, 2016 issued in PCT/JP2016/077667.

(Continued)

*Primary Examiner* — Nguyen T Truong
(74) *Attorney, Agent, or Firm* — Scully, Scott, Murphy & Presser, P.C.

(57) ABSTRACT

An imaging device includes: an image sensor including a plurality of pixels; a transmission cable configured to transmit power to the image sensor; a power source provided on a proximal end side of the transmission cable and configured to supply a voltage to the image sensor; a pulse signal superimposing unit provided on the proximal end side of the transmission cable and configured to superimpose a pulse signal on the voltage; a separator connected between the image sensor and the transmission cable and configured to separate an offset voltage and a pulse voltage from the voltage; a pulse signal detector connected between the separator and the transmission cable on a distal end side of the transmission cable and configured to detect the pulse signal superimposed on the offset voltage; and a timing generator configured to generate a driving signal based on the detected pulse signal.

7 Claims, 15 Drawing Sheets

(51) Int. Cl.
    *A61B 1/05*     (2006.01)
    *H04N 5/235*     (2006.01)
    *H04N 5/369*     (2011.01)
    *H04N 5/376*     (2011.01)
    *A61B 1/045*     (2006.01)
    *G02B 23/24*     (2006.01)
    *H04N 5/232*     (2006.01)
    *H04N 5/353*     (2011.01)
    *H04N 5/3745*     (2011.01)
    *H04N 7/18*     (2006.01)

(52) U.S. Cl.
    CPC ............ *A61B 1/05* (2013.01); *G02B 23/2484* (2013.01); *H04N 5/2253* (2013.01); *H04N 5/2353* (2013.01); *H04N 5/23203* (2013.01); *H04N 5/3532* (2013.01); *H04N 5/3698* (2013.01); *H04N 5/3745* (2013.01); *H04N 5/3765* (2013.01); *H04N 7/183* (2013.01); *H04N 2005/2255* (2013.01)

(58) Field of Classification Search
    CPC ............. H04N 5/23203; H04N 5/2353; H04N 5/3532; H04N 5/3698; H04N 5/3745; H04N 5/3765; H04N 7/183

USPC .......................................................... 348/65
See application file for complete search history.

(56) References Cited

U.S. PATENT DOCUMENTS

| | | |
|---|---|---|
| 2008/0192135 A1 | 8/2008 | Yamashita |
| 2009/0216080 A1 | 8/2009 | Nakamura |
| 2014/0320618 A1 | 10/2014 | Akahane et al. |
| 2015/0249798 A1 | 9/2015 | Nomoto et al. |
| 2015/0342443 A1 | 12/2015 | Tanabe et al. |

FOREIGN PATENT DOCUMENTS

| | | |
|---|---|---|
| JP | 2005260632 A | 9/2005 |
| JP | 2009164705 A | 7/2009 |
| JP | 2015-173738 A | 10/2015 |
| WO | 2014/171308 A1 | 10/2014 |

OTHER PUBLICATIONS

Extended Supplementary European Search Report dated Apr. 12, 2019 in European Patent Application No. 16 85 7217.0.

IMAGING DEVICE, ENDOSCOPE, AND ENDOSCOPE SYSTEM

CROSS-REFERENCE TO RELATED APPLICATIONS

This application is a continuation of PCT international application Ser. No. PCT/JP2016/077667 filed on Sep. 20, 2016 which designates the United States, incorporated herein by reference, and which claims the benefit of priority from Japanese Patent Application No. 2015-206637, filed on Oct. 20, 2015, incorporated herein by reference.

BACKGROUND

1. Technical Field

The disclosure relates to an imaging device, an endoscope, and an endoscope system for capturing a subject to generate image data of the subject.

2. Related Art

In recent years, as complementary metal oxide semiconductor (CMOS) image sensors are miniaturized, a connection area of an input/output (I/O) terminal for connecting a transmission cable occupies a large proportion against the entire chip area, so that reduction of the number of the I/O terminals becomes a new issue in miniaturization. Under such circumstances, JP 2009-164705 A discloses a technique of generating a synchronization signal from an image sensor in itself. Using this technique, the number of cables used to transmit the synchronization signal of the image sensor can be reduced, and the number of the I/O terminals can be reduced.

SUMMARY

In some embodiments, an imaging device includes: an image sensor including a plurality of pixels arranged in a two-dimensional matrix shape, each pixel being configured to receive external light and generate an imaging signal depending on an amount of the received light; a transmission cable configured to transmit power to the image sensor; a power source provided on a proximal end side of the transmission cable and configured to supply a voltage to the image sensor; a pulse signal superimposing unit provided on the proximal end side of the transmission cable and configured to superimpose a pulse signal on the voltage; a separator connected between the image sensor and the transmission cable and configured to separate an offset voltage and a pulse voltage from the voltage transmitted from the transmission cable and output the offset voltage to the image sensor; a pulse signal detector connected between the separator and the transmission cable on a distal end side of the transmission cable and configured to detect the pulse signal superimposed on the offset voltage; and a timing generator configured to generate, based on the pulse signal detected by the pulse signal detector, a driving signal for driving the image sensor.

In some embodiments, an endoscope includes: the imaging device; an insertion portion insertable into a subject; and a connector unit detachably installed in an image processing device configured to perform image processing for the imaging signal. The image sensor, the separator, the pulse signal detector, and the timing generator are provided on a distal end side of the insertion portion, and the power source and the pulse signal superimposing unit are provided in the connector unit.

In some embodiments, an endoscope system includes: the endoscope; and an image processing device configured to perform image processing for the imaging signal.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
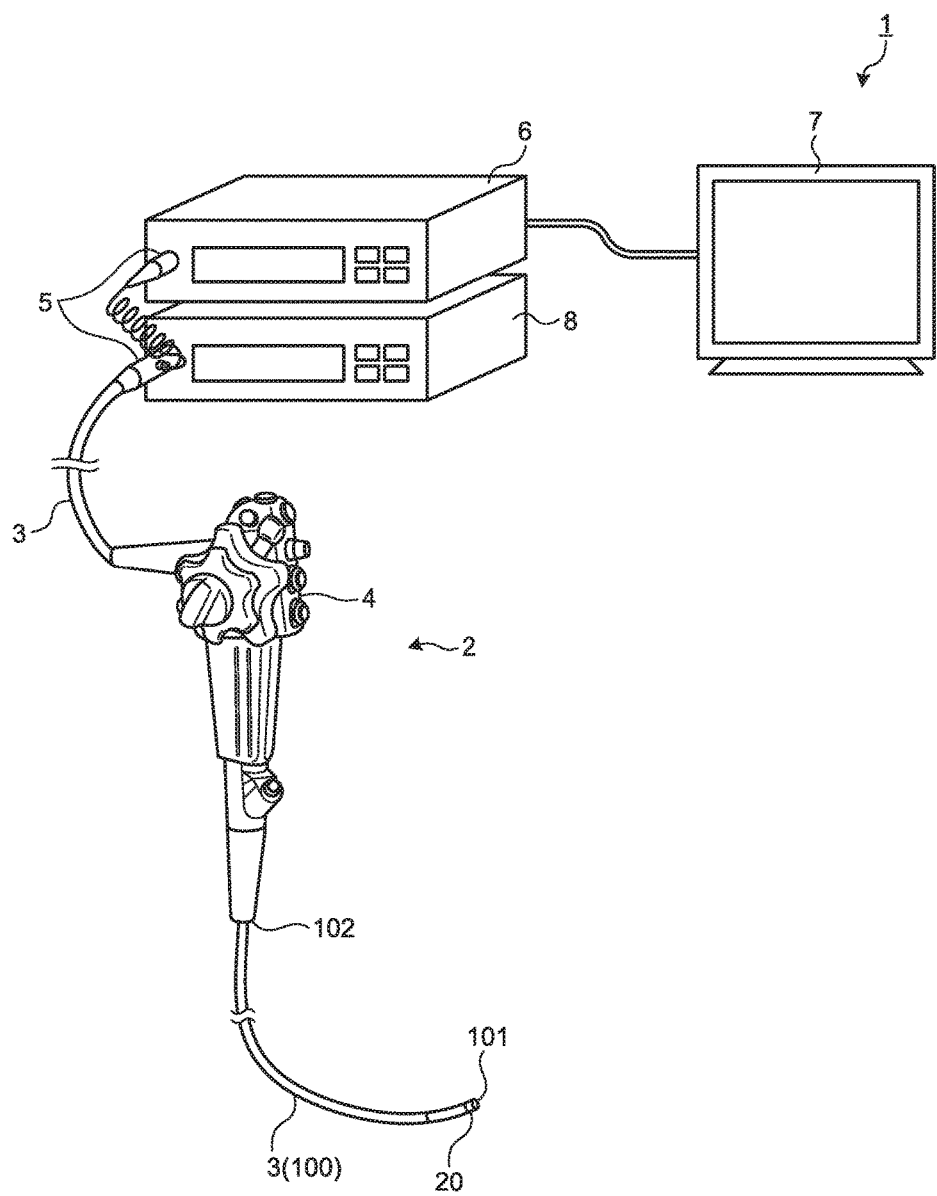
FIG. 1 is a schematic diagram schematically illustrating a whole configuration of an endoscope system according to a first embodiment of the disclosure.

Now, as an example of embodying the present invention (hereinafter, referred to as an "embodiment"), an endoscope system provided with an endoscope having an image sensor provided in a distal end of an insertion portion inserted into a subject will be described. Such an embodiment is not intended to limit the present invention. In addition, throughout the drawings, like reference numerals denote like elements. Furthermore, it is noticed that the drawings are merely for illustrative purposes, and they may be depicted in a way different from reality in terms of a relationship between thickness and width of each member, a scale of each member, or the like. Throughout the drawings, a part having a different scale or dimension may also be included.

First Embodiment

Configuration of Endoscope System

FIG. 1 is a schematic diagram schematically illustrating a whole configuration of the endoscope system according to a first embodiment of the disclosure. The endoscope system 1 of FIG. 1 includes an endoscope 2, a transmission cable 3, a connector unit 5, a processor 6 (image processing device), a display device 7, and a light source device 8.

The endoscope 2 captures an internal organ of a subject by inserting an insertion portion 100, which is a part of the transmission cable 3, into a body cavity of a subject and outputs an imaging signal (image data) to the processor 6. In addition, the endoscope 2 has an imaging unit 20 (imaging device) provided on a distal end 101 side of the insertion portion 100 inserted into a body cavity of a subject as one side end of the transmission cable 3 to capture an in-vivo image, and an operating unit 4 provided on a proximal end 102 side of the insertion portion 100 to receive various manipulations for the endoscope 2. The imaging signal of the image generated by the imaging unit 20 is output to the connector unit 5 through the transmission cable 3 having a length of, for example, several meters.

The transmission cable 3 connects the endoscope 2 and the connector unit 5 and connects the endoscope 2 and the light source device 8. In addition, the transmission cable 3 is used to transmit the imaging signal generated from the imaging unit 20 to the connector unit 5. The transmission cable 3 includes a cable, an optical fiber, and the like.

The connector unit 5 is connected to the endoscope 2, the processor 6, and the light source device 8 to perform a predetermined signal processing for the imaging signal output from the connected endoscope 2, convert the analog imaging signal to a digital imaging signal (A/D conversion), and output the digital imaging signal to the processor 6.

The processor 6 performs a predetermined image processing for the imaging signal input from the connector unit 5 and outputs the processed signal to the display device 7. In addition, the processor 6 totally controls the entire endoscope system 1. For example, the processor 6 performs control to change the illumination light emitted from the light source device 8 or to switch an imaging mode of the endoscope 2. Note that, according to the first embodiment, the processor 6 serves as an image processing device.

The display device 7 displays an image corresponding to the imaging signal subjected to the image processing of the processor 6. In addition, the display device 7 displays various types of information regarding the endoscope system 1. The display device 7 includes a display panel such as a liquid crystal display or an organic electro luminescence (EL) display.

The light source device 8 emits illumination light toward a subject from the distal end 101 side of the insertion portion 100 of the endoscope 2 through the connector unit 5 and the transmission cable 3. The light source device 8 includes a white light emitting diode (LED) that emits white light, an LED that emits special narrow bandwidth light having a wavelength band narrower than that of the white light, and the like. The light source device 8 emits the white light or the narrow bandwidth light toward the subject through the endoscope 2 under control of the processor 6.

Figure 2:
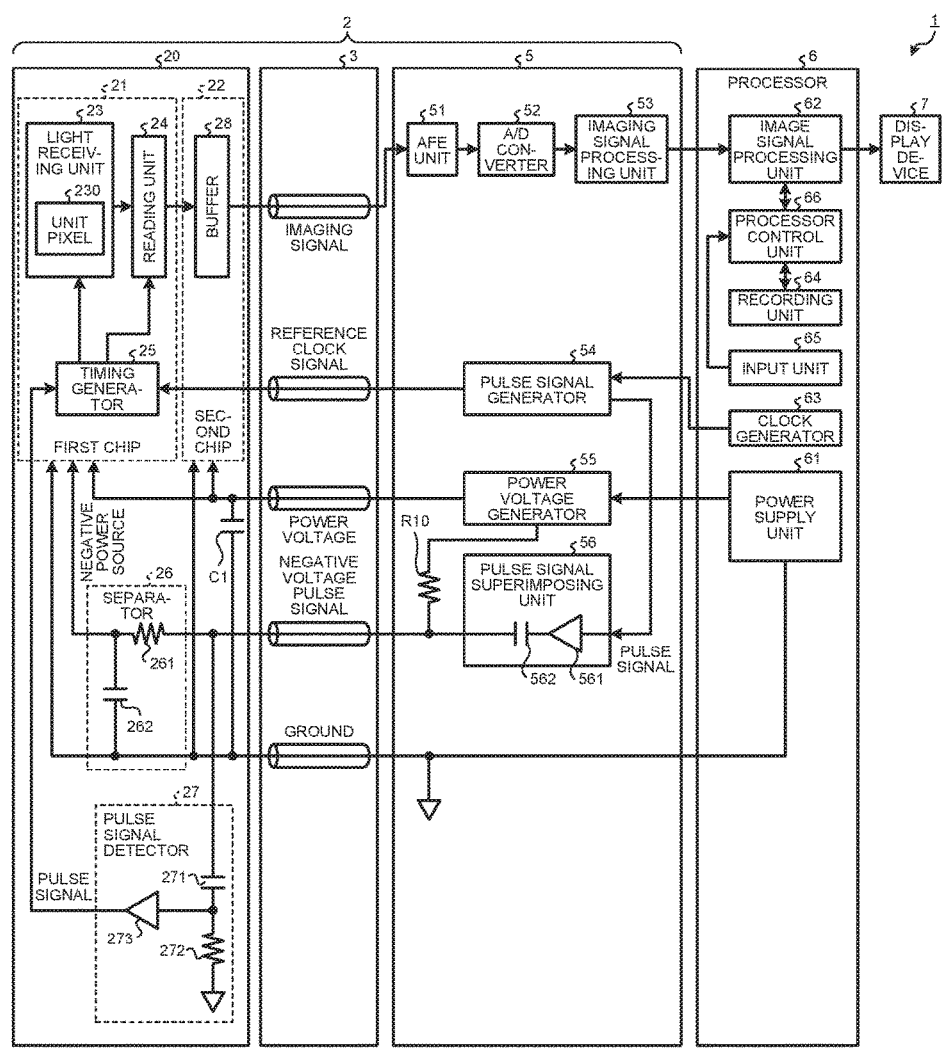
FIG. 2 is a block diagram illustrating functions of main parts of the endoscope system according to the first embodiment of the disclosure.

FIG. 2 is a block diagram illustrating functions of the main parts of the endoscope system 1. Configurations of each part of the endoscope system 1 and a path of an electric signal in the endoscope system 1 will be described in details with reference to FIG. 2.

Configuration of Endoscope

First, a configuration of the endoscope 2 will be described. The endoscope 2 illustrated in FIG. 2 has the imaging unit 20, the transmission cable 3, and the connector unit 5.

The imaging unit 20 has a first chip 21 (image sensor), a second chip 22, a separator 26 (AC component filter), and a pulse signal detector 27. A capacitor C1 for stabilizing a power voltage is provided between the power voltage VDD supplied to the imaging unit 20 and the ground GND.

The first chip 21 includes: a light receiving unit 23 having a plurality of unit pixels 230 arranged in a two-dimensional matrix shape, each pixel 230 being configured to receive external light and generate and output an imaging signal corresponding to the amount of the received light; a reading unit 24 configured to read the imaging signal photoelectrically converted in each of the unit pixels 230 of the light receiving unit 23; and a timing generator 25 configured to generate driving signals including a light receiving unit driving signal for driving the light receiving unit 23 and a reading unit driving signal for driving the reading unit 24 on the basis of a reference clock signal input from the connector unit 5 and a pulse signal input from the pulse signal detector 27 described below, and output the driving signals to the light receiving unit 23 and the reading unit 24. Note that the configuration of the first chip 21 will be described in more details below.

The second chip 22 has a buffer 28 configured to amplify the imaging signal output from each of the plurality of unit pixels 230 of the first chip 21 and output the amplified imaging signal to the transmission cable 3.

The separator 26 is connected between the first chip 21 and the transmission cable 3 to separate an offset voltage and a pulse voltage from a negative voltage transmitted from the transmission cable 3 and output the separated offset voltage to the first chip 21. The separator 26 includes a resistor 261 (for example, 100Ω) connected in series to the transmission cable 3 (signal line) used to transmit the negative voltage described below and a bypass capacitor 262 connected between a power voltage generator 55 described below and the ground GND. In the separator 26, an RC circuit (lowpass filter circuit) is constituted. As a result, a pulse signal of the pulse voltage superimposed on the negative voltage input from the connector unit 5 described below is cut off, and the offset voltage is output to the unit pixel 230.

The pulse signal detector 27 is connected between the separator 26 and a pulse signal superimposing unit 56 of the connector unit 5 described below by an AC coupling to detect a pulse signal (pulse voltage) superimposed on the negative voltage and output the detected pulse signal to the timing generator 25. Specifically, the pulse signal detector 27 is connected to the distal end side of the transmission cable 3 and the proximal end side of the resistor 261 of the separator 26. The pulse signal detector 27 includes a capacitor 271 connected to the transmission cable 3 (signal line) used to transmit the negative voltage, a resistor 272 having one end connected to the capacitor 271 and the other end connected to the ground GND, and an amplifier 273 configured to amplify the pulse signal extracted by the capacitor 271 and the resistor 272.

The transmission cable 3 includes at least five signal lines including a signal line for transmitting the power voltage generated by the power voltage generator 55 to the imaging unit 20, a signal line for transmitting the negative voltage generated by the power voltage generator 55 to the imaging unit 20, a signal line for transmitting the reference clock signal generated by a pulse signal generator 54 to the imaging unit 20, a signal line for transmitting the imaging signal generated by the imaging unit 20 to the connector unit 5, and a signal line for transmitting the ground GND to the imaging unit 20.

The connector unit 5 has an analog frontend portion 51 (hereinafter, referred to as an "AFE unit 51"), an A/D converter 52, an imaging signal processing unit 53, the pulse signal generator 54, the power voltage generator 55, and the pulse signal superimposing unit 56.

The AFE unit 51 receives the imaging signal transmitted from the imaging unit 20 and performs impedance matching using a passive element such as a resistor. Then, the AFE unit 51 extracts a pulse signal using a capacitor and determines an operational point using a voltage divider resistor. Then, the AFE unit 51 amplifies the imaging signal (analog signal) and outputs the amplified signal to the A/D converter 52.

The A/D converter 52 converts an analog imaging signal input from the AFE unit 51 into a digital imaging signal and outputs the digital imaging signal to the imaging signal processing unit 53.

The imaging signal processing unit 53 includes, for example, a field programmable gate array (FPGA) to perform various processes such as noise elimination and format transformation for the digital imaging signal input from the A/D converter 52 and output the processed imaging signal to the processor 6.

The pulse signal generator 54 generates a reference clock signal serving as a reference of the operation of each part of the imaging unit 20 on the basis of a clock signal (for example, 27 MHz clock signal) supplied from the processor 6 as a reference of the operation of each part of the endoscope 2, and outputs this reference clock signal to the timing generator 25 of the imaging unit 20 through the transmission cable 3. In addition, the pulse signal generator 54 outputs, to the pulse signal superimposing unit 56, a pulse signal for generating the driving signal of the imaging unit 20 on the basis of the clock signal supplied from the processor 6 as a reference of the operation of each part of the endoscope 2.

The power voltage generator 55 is provided on the proximal end side of the transmission cable 3 to generate the power voltage VDD necessary to drive the first and second chips 21 and 22 from the power supplied from the processor 6 and output the power voltage VDD to the first and second chips 21 and 22. In addition, the power voltage generator 55 generates a negative voltage necessary to drive the unit pixels 230 of the first chip 21 from the power supplied from the processor 6 and outputs the negative voltage to the first chip 21 through the transmission cable 3. The power voltage generator 55 generates the power voltage VDD and the negative voltage necessary to drive the first and second chips 21 and 22 using a regulator and the like. Note that, according to the first embodiment, the power voltage generator 55 serves as a negative power source.

The pulse signal superimposing unit 56 is provided on the proximal end side of the transmission cable 3 to amplify the pulse signal (for example, 0.5 V in the positive side) supplied from the pulse signal generator 54, superimpose this pulse signal on the transmission cable 3 used to transmit the negative voltage through the resistor R10, and output the superimposed signal to the imaging unit 20. The pulse signal superimposing unit 56 has an amplifier 561 configured to amplify the pulse signal supplied from the pulse signal generator 54 and a capacitor 562 for superimposing the pulse signal on the negative voltage.

Configuration of Processor

Next, a configuration of the processor 6 will be described.

The processor 6 is a control device for totally controlling the entire endoscope system 1. The processor 6 includes a power supply unit 61, an image signal processing unit 62, a clock generator 63, a recording unit 64, an input unit 65, and a processor control unit 66.

The power supply unit 61 generates a power voltage and supplies the generated power voltage to the power voltage generator 55 of the connector unit 5 along with the ground (GND).

The image signal processing unit 62 performs image processing such as synchronization, white balance (WB) adjustment, gain adjustment, gamma correction, digital-analog (D/A) conversion, and format transformation for the digital imaging signal subjected to the signal processing in the imaging signal processing unit 53 to convert the imaging signal into an image signal and output the image signal to the display device 7.

The clock generator 63 generates a clock signal serving as a reference of the operation of each part of the endoscope system 1 and outputs this clock signal to the pulse signal generator 54.

The recording unit 64 records various types of information regarding the endoscope system 1, data under processing, and the like. The recording unit 64 includes a recording medium such as a flash memory or a random access memory (RAM).

The input unit 65 receives various manipulation inputs regarding the endoscope system 1. For example, the input unit 65 receives an instruction signal input for changing the type of the illumination light emitted from the light source device 8. The input unit 65 includes, for example, a cross switch, a push button, and the like.

The processor control unit 66 totally controls each part of the endoscope system 1. The processor control unit 66 includes a central processing unit (CPU) and the like. The processor control unit 66 switches the illumination light emitted from the light source device 8 in response to the instruction signal input from the input unit 65.

By configuring the imaging unit 20 in this manner, the negative voltage supplied from the power voltage generator 55 is used to drive the unit pixels 230, so that a necessary electric current is reduced. Therefore, it is possible to supply the voltage from the bypass capacitor 262 of the separator 26 within a short time. Since the separator 26 has an RC circuit (lowpass filter circuit) formed by the bypass capacitor 262 and the resistor 261, the pulse signal is transmitted to the unit pixels 230 while being reduced sufficiently. In addition, the pulse signal detector 27 detects the pulse signal superimposed on the negative voltage by an AC coupling and outputs the pulse signal to the timing generator 25.

Specific Configuration of First Chip

Next, a specific configuration of the aforementioned first chip 21 will be described.

Figure 3:
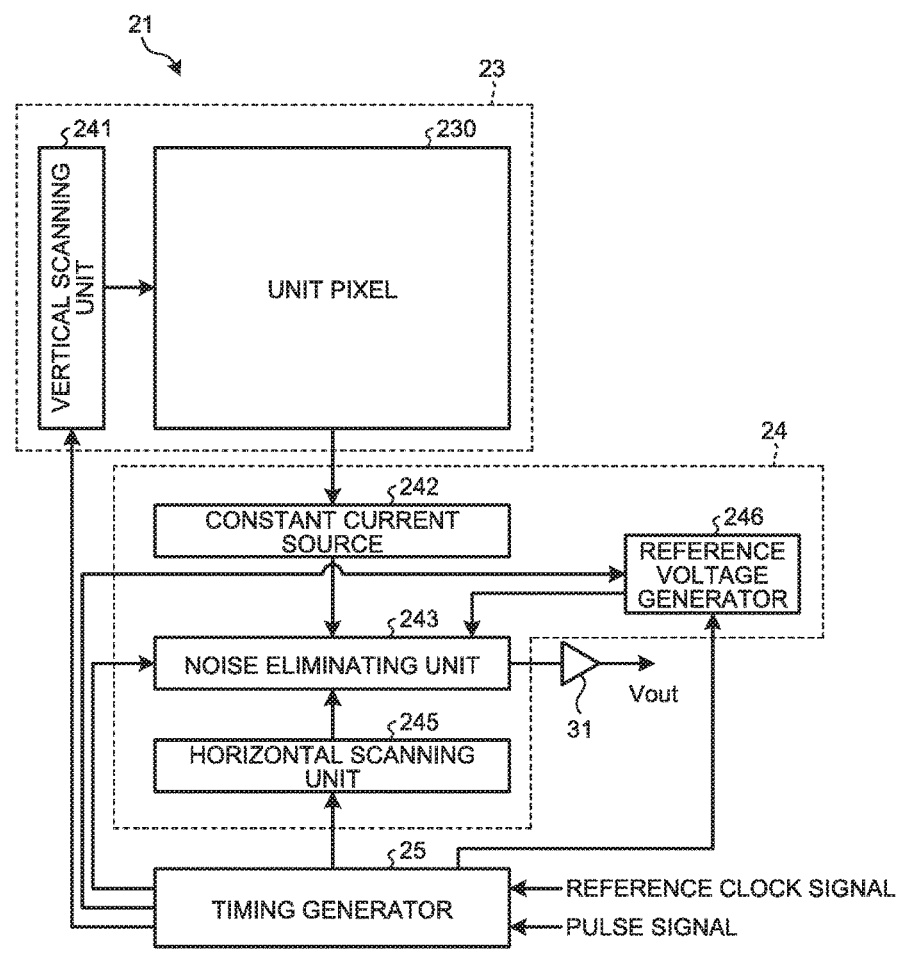
FIG. 3 is a block diagram illustrating a specific configuration of a first chip according to the first embodiment of the disclosure.
Figure 4:
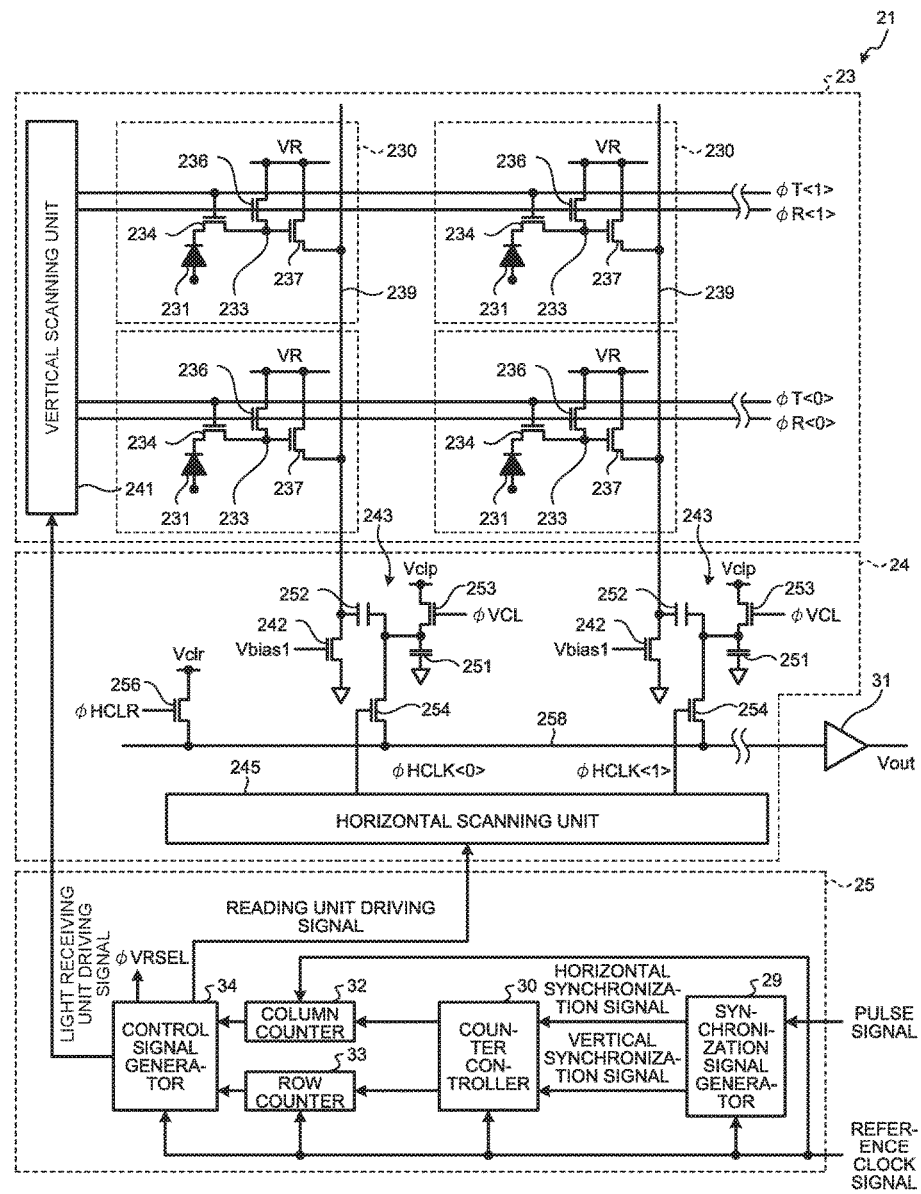
FIG. 4 is a circuit diagram illustrating a configuration of the first chip according to the first embodiment of the disclosure.

FIG. 3 is a block diagram illustrating a specific configuration of the first chip 21. FIG. 4 is a circuit diagram illustrating a configuration of the first chip 21.

As illustrated in FIGS. 3 and 4, the first chip 21 has a light receiving unit 23, a reading unit 24, a timing generator 25, and an output unit 31 (amplifier).

The timing generator 25 generates various driving signals ($\phi$, $\phi$R, $\phi$VCL, $\phi$HCLR, $\phi$HCLK, $\phi$VRSEL, and the like) on the basis of the pulse signal input from the pulse signal detector 27 and the reference clock signal from the connector unit 5 and outputs various driving signals to a vertical scanning unit 241, a noise eliminating unit 243, a horizontal scanning unit 245, and a reference voltage generator 246. The timing generator 25 includes a synchronization signal generator 29, a counter controller 30, a column counter 32, a row counter 33, and a control signal generator 34.

The synchronization signal generator 29 receives the reference clock signal and the coded pulse signal from the connector unit 5 through the transmission cable 3, decodes the coded pulse signal to generate horizontal and vertical synchronization signals, and outputs the generated horizontal and vertical synchronization signals to the counter controller 30.

The counter controller 30 outputs a reset signal to the column counter 32 on the basis of the reference clock signal input from the connector unit 5 and the horizontal synchronization signal input from the synchronization signal generator 29. In addition, the counter controller 30 outputs a reset signal to the row counter 33 on the basis of the reference clock signal input from the connector unit 5 and the vertical synchronization signal input from the synchronization signal generator 29. In addition, the counter controller 30 monitors a column counter value of the column counter 32. When the column counter value reaches a predetermined counter value, the counter controller 30 outputs a count-up signal to the row counter 33.

The column counter 32 counts up the column counter value at every predetermined period on the basis of the reference clock signal input from the connector unit 5, and outputs the incremented column counter value to a control signal generator 34. In addition, the column counter 32 resets the column counter value when the reset signal is input from the counter controller 30.

The row counter 33 counts up the row counter value on the basis of the reference clock signal input from the connector unit 5 and the count-up signal input from the counter controller 30 and outputs the incremented row counter value to the control signal generator 34. In addition, the row counter 33 resets the row counter value when the reset signal is input from the counter controller 30.

The control signal generator 34 generates a light receiving unit driving signal (for example, $\phi$T and $\phi$R) on the basis of the reference clock signal input from the connector unit 5 and the row counter value input from the row counter 33, applies a row shift pulse, and outputs the resulting signal to the vertical scanning unit 241. In addition, the control signal generator 34 generates a reading unit driving signal (for example, $\phi$HCLK) on the basis of the reference clock signal input from the connector unit 5 and the column counter value input from the column counter 32, applies a column shift pulse, and outputs the resulting signal to the horizontal scanning unit 245. Furthermore, the control signal generator 34 generates driving signals (such as $\phi$VCL, $\phi$HCLR, and $\phi$VRSEL) on the basis of the reference clock signal input from the connector unit 5, the horizontal synchronization signal, and the vertical synchronization signal, and outputs the driving signals to the noise eliminating unit 243, a horizontal reset transistor 256, and the reference voltage generator 246.

The vertical scanning unit 241 applies a row selection pulse $\phi$T<M> and $\phi$R<M> to the selected rows <M> (where "M=0, 1, 2, . . . , m−1, m") of the light receiving unit 23 on the basis of the driving signal ($\phi$T and $\phi$R) supplied from the timing generator 25 to drive each unit pixel 230 of the light receiving unit 23 using a constant current source 242, transmits the imaging signal and the noise signal for pixel reset operation to a vertical transmission line 239 (first transmission line), and outputs the imaging signal and the noise signal to the noise eliminating unit 243.

The reading unit 24 has the constant current source 242, a noise eliminating unit 243, a horizontal scanning unit (column selector) 245, and a reference voltage generator 246.

The noise eliminating unit 243 removes an output variation in each unit pixel 230 and a noise signal for the pixel reset operation and outputs the imaging signal photoelectrically converted by each unit pixel 230. Note that the noise eliminating unit 243 will be described in more details below.

The horizontal scanning unit 245 applies the column selection pulse $\phi$HCLK<N> to the selected column <N> (where "N=0, 1, 2, . . . , n−1, n) of the light receiving unit 23 on the basis of the driving signal ($\phi$HCLK) supplied from the timing generator 25, transmits the imaging signal photoelectrically converted by each unit pixel 230 to a horizontal transmission line 258 (second transmission line) through the noise eliminating unit 243, and outputs the imaging signal to the output unit 31.

A plurality of unit pixels 230 are arranged in the light receiving unit 23 of the first chip 21 in a two-dimensional matrix shape. Each unit pixel 230 includes a photoelectric conversion element 231 (photodiode), a charge-voltage converter 233, a transfer transistor 234 (first transfer portion), a charge-voltage converter reset unit 236 (transistor), and a pixel output transistor 237 (signal output unit). Note that, herein, one or a plurality of photoelectric conversion elements and the transfer transistor for transferring signal charges from each photoelectric conversion element to the charge-voltage converter 233 will be referred to as a "unit cell." That is, the unit cell includes a set of one or a plurality of photoelectric conversion elements and the transfer transistor, and each unit pixel 230 has a single unit cell.

According to this embodiment, pixel sharing is not performed, and the unit cell has a single photoelectric conversion element. Alternatively, the unit cell may include a set of photoelectric conversion elements. In this case, for example, the unit cell may be formed by combining two photoelectric conversion elements neighboring in the column direction into a single set or by combining two photoelectric conversion elements neighboring in the row direction into a single set. Alternatively, the unit cell may be formed by combining four photoelectric conversion elements neighboring in the row and column directions into a single set.

The photoelectric conversion element 231 photoelectrically converts incident light into a signal charge amount corresponding to the amount of the incident light and accumulates the charges. A cathode of the photoelectric conversion element 231 is connected to one end side of the transfer transistor 234, and an anode side is connected to the ground GND.

The charge-voltage converter 233 includes a floating diffusion capacitance (FD) to convert the electric charges accumulated in the photoelectric conversion element 231 into a voltage.

The transfer transistor 234 transfers electric charges from the photoelectric conversion element 231 to the charge-voltage converter 233. The transfer transistor 234 has a gate connected to the signal line supplied with the driving pulse φT, one end connected to the photoelectric conversion element 231, and the other end connected to the charge-voltage converter 233. If the driving pulse φT becomes HIGH through the signal line from the vertical scanning unit 241, the transfer transistor 234 is turned on to transfer the signal charge from the photoelectric conversion element 231 to the charge-voltage converter 233. If the driving pulse φT becomes LOW, the transfer transistor 234 is turned off and accumulates charges. The HIGH side voltage of the driving pulse φT is supplied from the power voltage generator 55 through the transmission cable 3. In addition, the LOW side voltage of the driving pulse φT is supplied with the negative voltage with a pulse signal being removed by the separator 26.

The charge-voltage converter reset unit 236 resets the charge-voltage converter 233 to a predetermined electric potential. The charge-voltage converter reset unit 236 has one end connected to the variable voltage VR, the other end connected to the charge-voltage converter 233, a gate connected to the signal line supplied with the driving pulse φR. When the driving pulse φR becomes HIGH from the vertical scanning unit 241 through the signal line, the charge-voltage converter reset unit 236 is turned on so that the signal charges accumulated in the charge-voltage converter 233 are discharged, and the charge-voltage converter 233 is reset to a predetermined electric potential. When the driving pulse φR becomes LOW, the charge-voltage converter reset unit 236 is turned off, so that the charge-voltage converter 233 has a charge-accumulatable state. The HIGH side voltage of the driving pulse φR is supplied from the power voltage generator 55 through the transmission cable 3. In addition, the LOW side voltage is supplied with the negative voltage with a pulse signal being removed by the separator 26.

The pixel output transistor 237 outputs the imaging signal subjected to the voltage conversion by the charge-voltage converter 233 to a vertical transmission line 239. The pixel output transistor 237 has one end connected to the variable voltage VR, the other end connected to the vertical transmission line 239, and a gate connected to the charge-voltage converter 233. The pixel output transistor 237 is turned on or off depending on a combination of a level of the variable voltage VR and the charge-voltage converter reset unit 236 to selectively transmit the imaging signal to the vertical transmission line 239.

According to the first embodiment, if the variable voltage VR has a power voltage VDD level (for example, 3.3 V), and the driving signal φR is supplied to the gate of the charge-voltage converter reset unit 236, the pixel output transistor 237 is turned on, so that a unit pixel including this charge-voltage converter reset unit 236 is selected (selection operation). In addition, if the variable voltage VR has a deselection voltage level Vfd_L (for example, 1 V), and the driving signal φR is supplied to the gate of the charge-voltage converter reset unit 236, the pixel output transistor 237 is turned off, so that the unit pixel including the charge-voltage converter reset unit 236 is deselected (deselection operation).

The constant current source 242 has one end connected to the vertical transmission line 239, the other end connected to the ground GND, and a gate applied with a bias voltage Vbias1. The unit pixel 230 is driven by the constant current source 242 to read out the output of the unit pixel 230 to the vertical transmission line 239. The signal read to the vertical transmission line 239 is input to the noise eliminating unit 243.

The noise eliminating unit 243 has an AC-coupled transfer capacitance 252 (AC-coupling capacitor) having one end connected to the vertical transmission line 239, a sampling capacitance 251 (charge accumulation capacitor) connected between the other end of the transfer capacitance 252 and the ground GND, and a clamp switch 253 (voltage clamping transistor) connected to a connection node between the transfer capacitance 252 and the sampling capacitance 251. Note that the connection node is connected to one end of a column selection switch 254.

If the variable voltage VR has the power voltage VDD level, and the driving signal φR is supplied to the gate of the charge-voltage converter reset unit 236, the noise signal is read to the vertical transmission line 239 and is transferred by the transfer capacitance 252. Then, if the driving signal φVCL is input to the gate of the clamp switch 253 from the timing generator 25, the noise signal level is sampled by the sampling capacitance 251 through the clamp switch 253 (by switching the clamp switch 253 from ON to OFF). Then, in the event of reading of the imaging signal, the imaging signal including the noise signal (optical noise sum signal) is transferred by the transfer capacitance 252 again. A voltage variation corresponding to the imaging signal subjected to the pixel reset operation is transferred. As a result, it is possible to extract the imaging signal with the noise signal being subtracted from the optical noise sum signal.

The horizontal reset transistor 256 has one end connected to the horizontal reset voltage Vclr, the other end connected to the horizontal transmission line 258, and a gate to which the driving signal φHCLR is input from the timing generator 25. When the driving signal φHCLR is input to the gate of the horizontal reset transistor 256 from the timing generator 25, the horizontal reset transistor 256 is turned on, and the horizontal transmission line 258 is reset.

The column selection switch 254 has one end connected to the other end of the transfer capacitance 252 through a connection node between the transfer capacitance 252 and the sampling capacitance 251, the other end connected to the horizontal transmission line 258 (second transmission line), and a gate connected to the signal line for supplying the driving signal φHCLK<N> from the horizontal scanning unit 245. When the driving signal φHCLK<N> is supplied from the horizontal scanning unit 245 to the gate of the column selection switch 254 of the column <N>, the column <N> of the column selection switch 254 is turned on, so that the signal of the vertical transmission line 239 of the column <N> (the imaging signal with a noise being removed by the noise eliminating unit 243) is transmitted to the horizontal transmission line 258.

The horizontal transmission line 258 transmits the signal read through the column selection switch 254 to the output unit 31.

The output unit 31 amplifies the imaging signal subjected to the noise elimination as necessary and outputs the amplified signal to the second chip 22.

The second chip 22 transmits the imaging signal subjected to the noise elimination to the connector unit 5 through the transmission cable 3.

Figure 5:
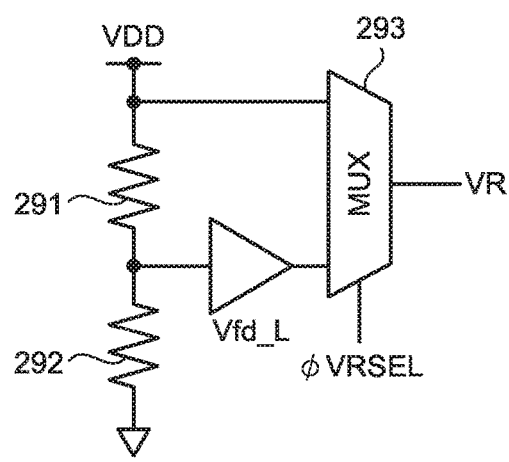
FIG. 5 is a circuit diagram illustrating a configuration of a reference voltage generator of the endoscope system according to the first embodiment of the disclosure.

FIG. 5 is a circuit diagram illustrating a configuration of the reference voltage generator 246 of the endoscope system 1. The reference voltage generator 246 (constant voltage signal generator) includes a resistor voltage divider circuit having a pair of resistors 291 and 292 and a multiplexer 293 driven by the driving signal φVRSEL.

The multiplexer 293 applies the variable voltage VR to all of the pixels by alternately switching between the power voltage VDD and the deselection voltage Vfd_L generated from the resistor voltage divider circuit on the basis of the driving signal φVRSEL input from the timing generator 25.

Figure 6:
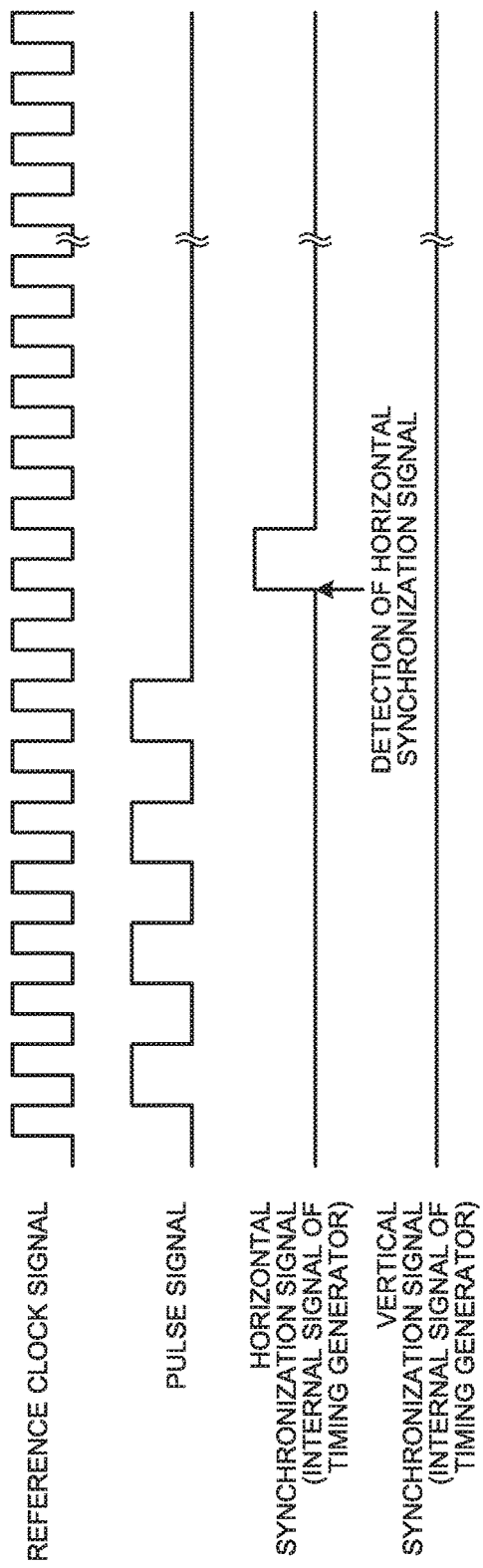
FIG. 6 is a timing chart illustrating operations performed to detect a horizontal synchronization signal using a timing generator according to the first embodiment of the disclosure.

Detection Operation for Horizontal Synchronization Signal Using Timing Generator Next, a detection operation of the horizontal synchronization signal using the timing generator 25 will be described. FIG. 6 is a timing chart illustrating operations performed to detect the horizontal synchronization signal using the timing generator 25. In FIG. 6, the reference clock signal, the pulse signal, the decoded horizontal synchronization signal, and the decoded vertical synchronization signal (frame synchronization signal) are illustrated in order from the top.

As illustrated in FIG. 6, if the reference clock signal is input from the connector unit 5, and the pulse signal is input from the pulse signal detector 27, the synchronization signal generator 29 detects the horizontal synchronization signal by decoding the pulse signal input from the pulse signal detector 27 and outputs the detected horizontal synchronization signal to the counter controller 30.

Subsequently, if the horizontal synchronization signal is input from the synchronization signal generator 29, the counter controller 30 outputs a column counter reset signal to the column counter 32.

Then, if the column counter reset signal is input from the counter controller 30, the column counter 32 resets a column count value in synchronization with a falling edge of the column counter reset signal.

Subsequently, the control signal generator 34 monitors the column counter value, generates the light receiving unit driving signal and the reading unit driving signal on the basis of the counter value incremented by the reference clock signal, and outputs the light receiving unit driving signal and the reading unit driving signal to the vertical scanning unit 241 and the horizontal scanning unit 245, respectively, so that an imaging signal corresponding to a single row is output from the output unit 31.

Then, the control signal generator 34 halts the operation until the synchronization signal generator 29 decodes the next horizontal synchronization signal on the basis of the pulse signal input from the pulse signal detector 27.

Detection Operation for Vertical Synchronization Signal Using Timing Generator

Figure 7:
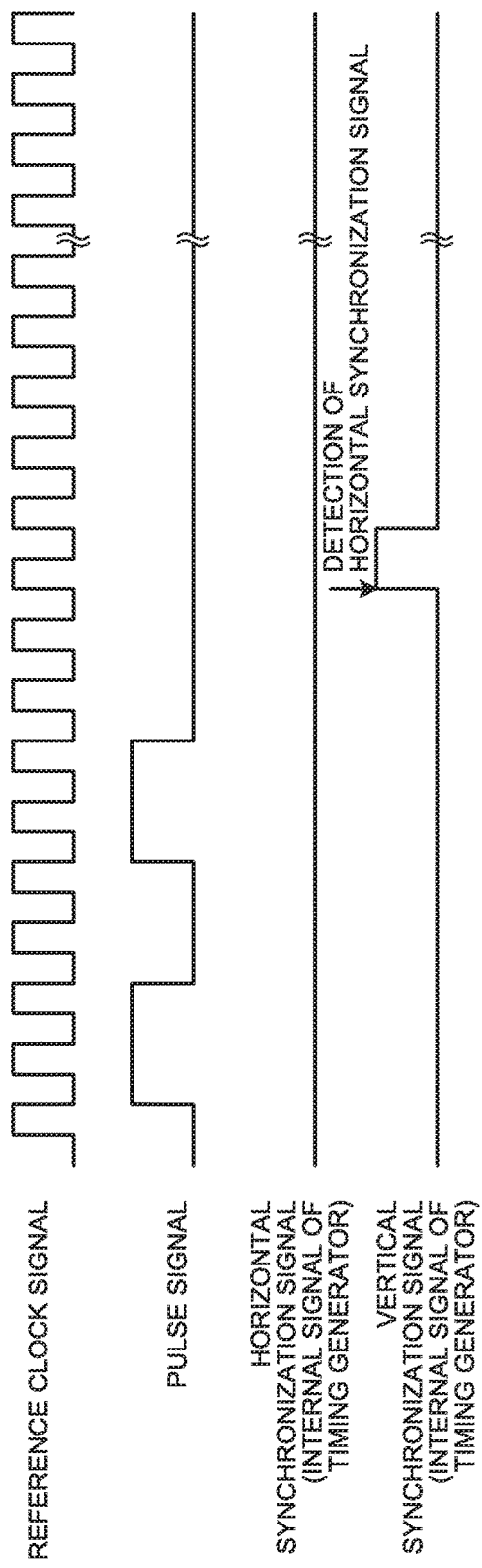
FIG. 7 is a timing chart illustrating operations performed to detect a vertical synchronization signal using the timing generator according to the first embodiment of the disclosure.

Next, a detection operation for the vertical synchronization signal using the timing generator 25 will be described. FIG. 7 is a timing chart illustrating operations performed to detect the vertical synchronization signal using the timing generator 25. In FIG. 7, the reference clock signal, the pulse signal, the decoded horizontal synchronization signal, and the decoded vertical synchronization signal are illustrated in order from the top.

As illustrated in FIG. 7, if the reference clock signal is input from the connector unit 5, and the pulse signal is input from the pulse signal detector 27, the synchronization signal generator 29 decodes the pulse signal input from the pulse signal detector 27 to detect the vertical synchronization signal and outputs the detected vertical synchronization signal to the counter controller 30.

Subsequently, if the vertical synchronization signal is input from the synchronization signal generator 29, the counter controller 30 outputs the row counter reset signal to the row counter 33.

Then, if the row counter reset signal is input from the counter controller 30, the row counter 33 resets the row count in synchronization with a falling edge of the row counter reset signal.

Subsequently, the control signal generator 34 monitors the row counter value and sequentially selects the rows of the light receiving unit 23 on the basis of the counter value incremented by the reference clock signal, so that the imaging signal corresponding to one frame is output to the output unit 31.

Then, the control signal generator 34 halts the operation until the synchronization signal generator 29 decodes the next vertical synchronization signal on the basis of the pulse signal input from the pulse signal detector 27.

According to the first embodiment of the disclosure described above, the pulse signal detector 27 detects the pulse signal superimposed on the transmission cable 3 used to transmit the negative voltage and outputs the detection result to the timing generator 25. Therefore, it is possible to reduce the number of the I/O terminals while receiving the control signal.

According to the first embodiment of the disclosure, the pulse signal superimposing unit 56 outputs the pulse signal for generating the synchronization signal for driving the imaging unit 20 to the imaging unit 20 by superimposing it on the transmission cable 3 used to transmit the negative voltage. Therefore, it is possible to reduce the number of transmission cables 3 used to connect the imaging unit 20 and the connector unit 5.

According to the first embodiment of the disclosure, the synchronization signal generator 29 provided in the imaging unit 20 of the distal end 101 side generates the horizontal synchronization signal and the vertical synchronization signal on the basis of the pulse signal superimposed on the pulse signal superimposing unit 56 and the reference clock signal, and transmits the vertical synchronization signal and the horizontal synchronization signal to the vertical scanning unit 241 and the horizontal scanning unit 245. Therefore, it is possible to reduce the number of the transmission cables 3 used to generate the synchronization signal.

According to the first embodiment of the disclosure, even when an abnormality occurs in the imaging unit 20, the pulse signal superimposing unit 56 transmits the pulse signal through the transmission cable 3 used to transmit the negative voltage, so that the counter can be reset. Therefore, it is possible to enable recovery to a normal operation. As a result, according to the first embodiment of the disclosure, it is possible to prevent a failure in which the image is displayed intermittently even when an abnormality occurs in the imaging unit 20 during medical operation for a subject by an operator such as a doctor.

According to the first embodiment of the disclosure, since the separator 26 and the pulse signal detector 27 are integrated into the second chip 22, it is possible to further miniaturize the imaging unit 20.

Modification of First Embodiment

Next, a modification of the first embodiment of the disclosure will be described. In the modification of the first embodiment, a pulse signal is superimposed on a negative side (minus (−) side) for the negative voltage. For this reason, the modification is different from the first embodiment in the configuration of the imaging unit 20. In the following description, a configuration of the imaging unit relating to this modification of the first embodiment will be described. Note that like reference numerals denote like elements as in the first embodiment, and they will not be repeatedly described.

Figure 8:
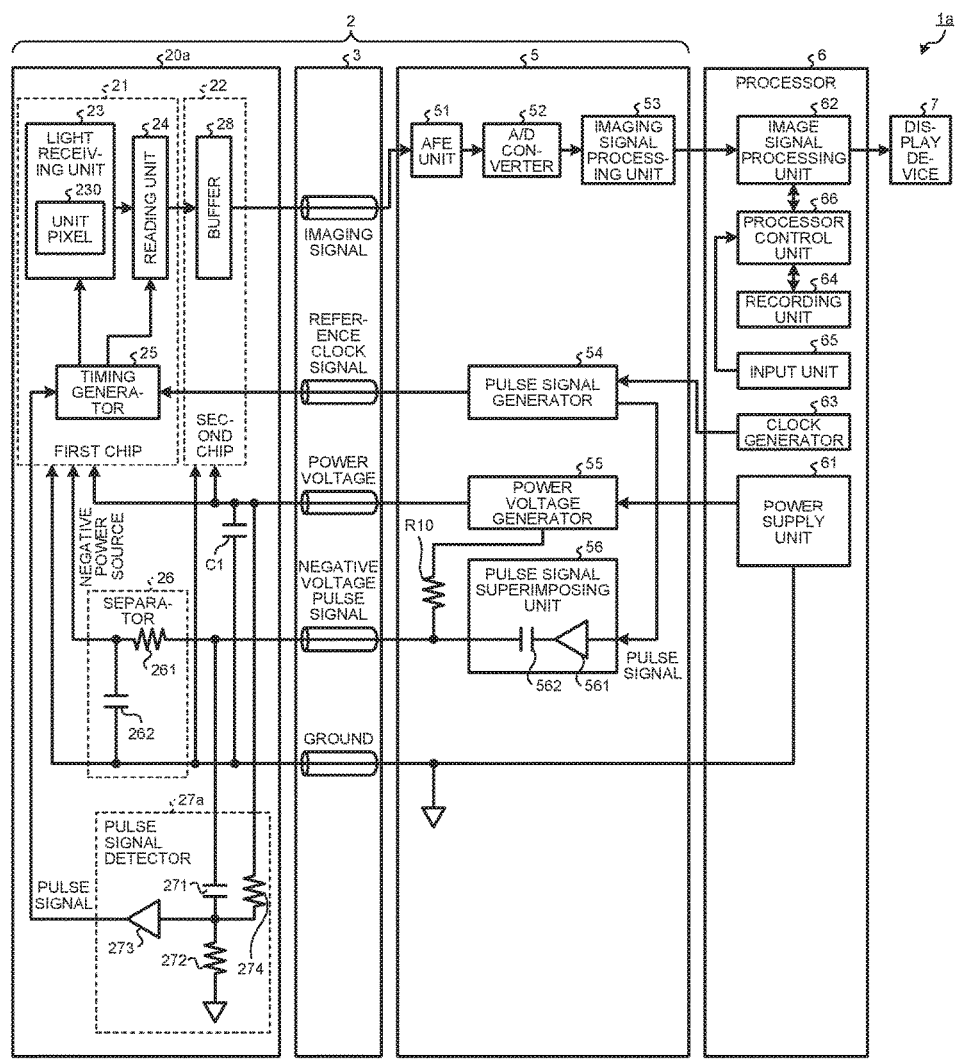
FIG. 8 is a block diagram illustrating functions of main parts of an endoscope system according to a modification of the first embodiment of the disclosure.

FIG. 8 is a block diagram illustrating functions of main parts of an endoscope system according to the modification of the first embodiment of the disclosure. The endoscope system 1a of FIG. 8 is provided with an imaging unit 20a instead of the imaging unit 20 of the endoscope system 1 of the first embodiment described above.

The imaging unit 20a is provided with a pulse signal detector 27a instead of the pulse signal detector 27 of the imaging unit 20 of the first embodiment described above. In addition, the imaging unit 20a further has a resistor 274 provided between the power voltage VDD and the pulse signal detector 27a.

In the modification of the first embodiment of the disclosure described above, it is possible to provide the effects similar to those of the first embodiment. Therefore, it is possible to reduce the number of the transmission cables 3 while receiving the control signal.

Second Embodiment

Next, a second embodiment of the disclosure will be described. The endoscope system according to the second embodiment is different from the endoscope system 1 of the first embodiment in the configuration of the first chip 21 and the operation of the timing generator 25. In the following description, the first chip of the endoscope system according to the second embodiment will be described first, and the operation of the timing generator will be described. Note that like reference numerals denote like elements as in the first embodiment described above, and they will not be repeatedly described.

Specific Configuration of First Chip

Figure 9:
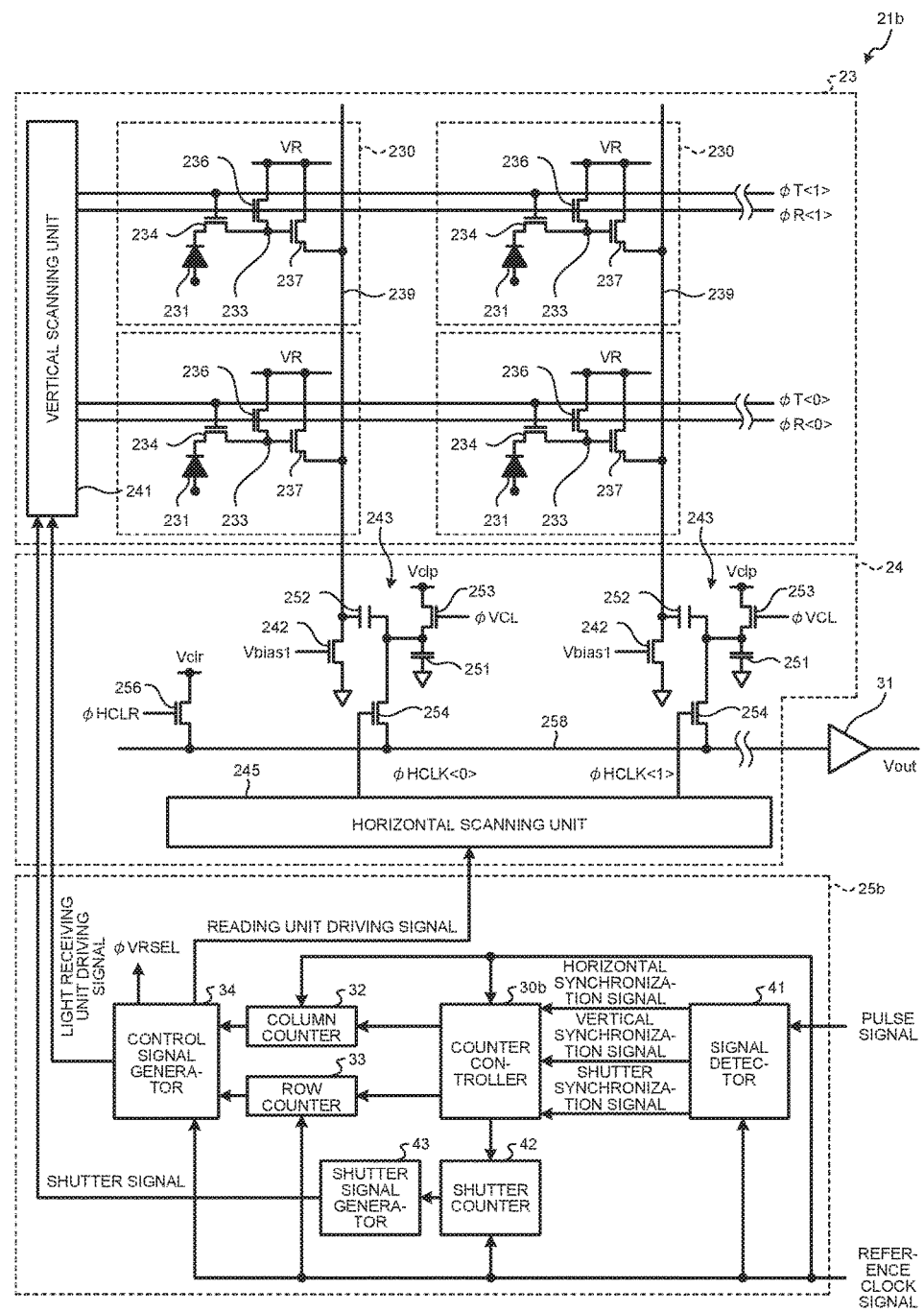
FIG. 9 is a circuit diagram illustrating a configuration of a first chip according to a second embodiment of the disclosure.

FIG. 9 is a circuit diagram illustrating a configuration of a first chip according to the second embodiment of the disclosure. The first chip 21b of FIG. 9 is provided with a timing generator 25b instead of the timing generator 25 of the first chip 21 of the first embodiment described above.

The timing generator 25b generates various driving signals (such as φT, φR, φVCL, φHCLR, φHCLK, and φVRSEL) on the basis of the pulse signal input from the pulse signal detector 27 and the reference clock signal from the connector unit 5, and outputs the driving signals to the vertical scanning unit 241, the noise eliminating unit 243, the horizontal scanning unit 245, and the reference voltage generator 246. The timing generator 25b is provided with a signal detector 41 and a counter controller 30b instead of the synchronization signal generator 29 of the timing generator 25 and the counter controller 30 of the first embodiment described above. In addition, the timing generator 25b further has a shutter counter 42 and a shutter signal generator 43.

The signal detector 41 receives the reference clock signal and the coded pulse signal from the connector unit 5 through the transmission cable 3, decodes the coded pulse signal to generate a horizontal synchronization signal, a vertical synchronization signal, and a shutter synchronization signal, and outputs the generated horizontal synchronization signal, vertical synchronization signal, and shutter synchronization signal to the counter controller 30b.

The counter controller 30b outputs a reset signal to the column counter 32 on the basis of the reference clock signal input from the connector unit 5 and the horizontal synchronization signal input from the signal detector 41. In addition, the counter controller 30b outputs a reset signal to the row counter 33 on the basis of the reference clock signal input from the connector unit 5 and the vertical synchronization signal input from the signal detector 41. In addition, the counter controller 30b outputs a reset signal to the shutter counter 42 on the basis of the reference clock signal input from the connector unit 5 and the shutter synchronization signal input from the signal detector 41. Furthermore, the counter controller 30b monitors the column counter value of the column counter 32. If the column counter value reaches a predetermined counter value, the counter controller 30b outputs a count-up signal to the row counter 33.

The shutter counter 42 counts up the shutter counter value on the basis of the reference clock signal input from the connector unit 5 and the count-up signal input from the counter controller 30b and outputs the incremented shutter counter value to the shutter signal generator 43. In addition, the shutter counter 42 resets the shutter counter value when a reset signal is input from the counter controller 30b.

The shutter signal generator 43 generates a light receiving unit driving signal (for example, φT and φR) on the basis of the shutter counter value input from the shutter counter 42, and outputs the light receiving unit driving signal to the vertical scanning unit 241. Note that, according to the second embodiment, the shutter signal generator 43 serves as a driving signal generator for generating the driving signal.

Detection Operation for Shutter Synchronization Signal Using Timing Generator

Figure 10:
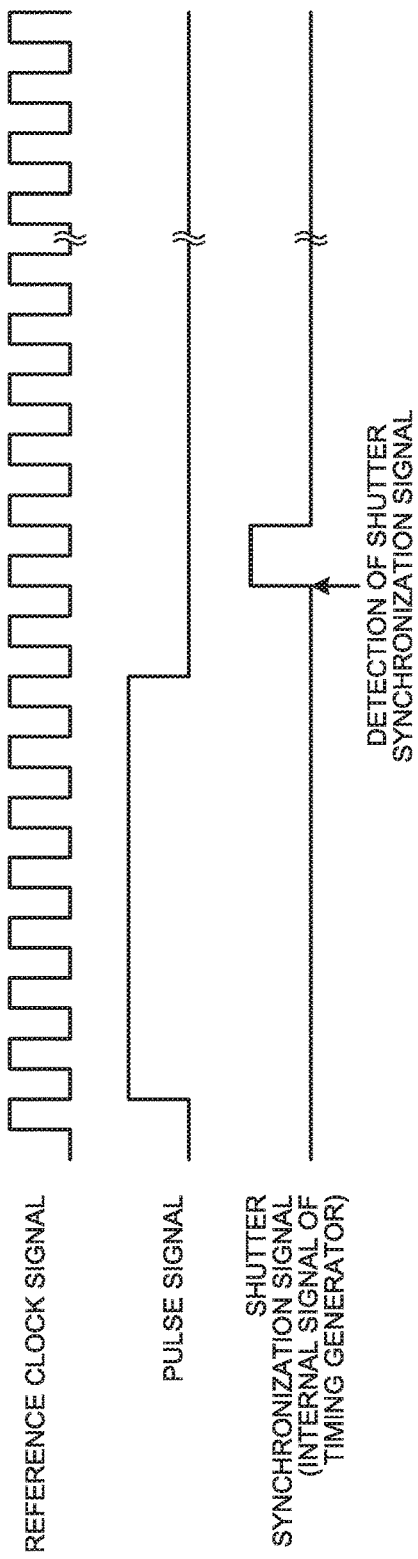
FIG. 10 is a timing chart illustrating operations performed to detect a shutter synchronization signal using a timing generator according to the second embodiment of the disclosure.
Figure 11:
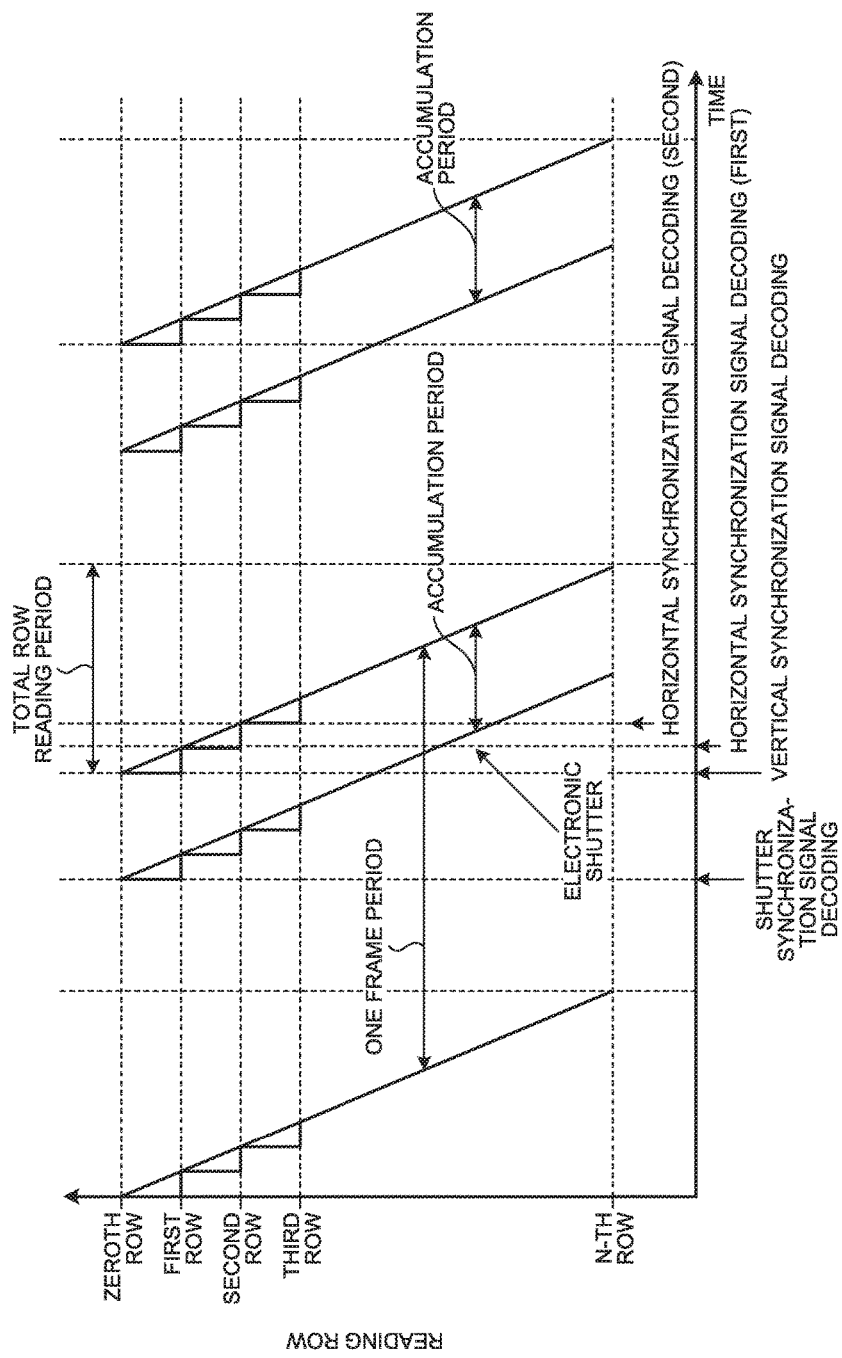
FIG. 11 is a diagram schematically illustrating a timing at which a reading unit reads an imaging signal from each unit pixel of a light receiving unit under control of the timing generator according to the second embodiment of the disclosure.

Next, a detection operation for the shutter synchronization signal using the timing generator 25b will be described. FIG. 10 is a timing chart illustrating operations performed to detect the shutter synchronization signal using the timing generator 25b. FIG. 11 is a diagram schematically illustrating timings at which the reading unit 24 reads the imaging signal from each unit pixel 230 of the light receiving unit 23 under control of the timing generator 25b. In FIG. 10, the reference clock signal, the pulse signal, and the shutter synchronization signal are illustrated in order from the top.

As illustrated in FIG. 10, if the reference clock signal is input from the connector unit 5, and the pulse signal is input from the pulse signal detector 27, the signal detector 41 detects the shutter synchronization signal by decoding the pulse signal input from the pulse signal detector 27.

Subsequently, if the shutter synchronization signal is input from the signal detector 41 (in FIG. 11, SHUTTER SYNCHRONIZATION SIGNAL DECODING), the counter controller 30b outputs the shutter synchronization signal to the shutter counter 42.

Then, when a shutter counter reset signal is input from the counter controller 30b, the shutter counter 42 resets the shutter counter value in synchronization with a falling edge of the shutter counter reset signal.

Subsequently, the shutter signal generator 43 monitors the shutter counter value, generates the light receiving unit driving signal on the basis of the shutter counter value incremented by the reference clock signal, and outputs the generated light receiving unit driving signal to the vertical scanning unit 241. As a result, the first chip 21b of FIG. 9 performs a rolling shutter operation. In this case, when the vertical synchronization signal is input (in FIG. 11, VERTICAL SYNCHRONIZATION SIGNAL DECODING), the row counter 33 and the column counter 32 of the first embodiment described above are reset, and reading of the imaging signal from the light receiving unit 23 starts (HORIZONTAL SYNCHRONIZATION SIGNAL DECODING (FIRST) →HORIZONTAL SYNCHRONIZATION SIGNAL DECODING (SECOND)). However, the shutter counter 42 is not reset.

According to the second embodiment of the disclosure described above, it is possible to reduce the number of the transmission cables 3 while receiving the control signal.

Third Embodiment

Next, a third embodiment of the disclosure will be described. An endoscope system according to the third embodiment is different from the endoscope system of the second embodiment in the configuration of the first chip 21b and the operation of the timing generator 25b. In the following description, the configuration of the first chip of the endoscope system according to the third embodiment will be described first, and the operation of the timing generator will be described. Note that like reference numerals denote like elements as in the first embodiment described above, and they will not be repeatedly described.

Configuration of First Chip

Figure 12:
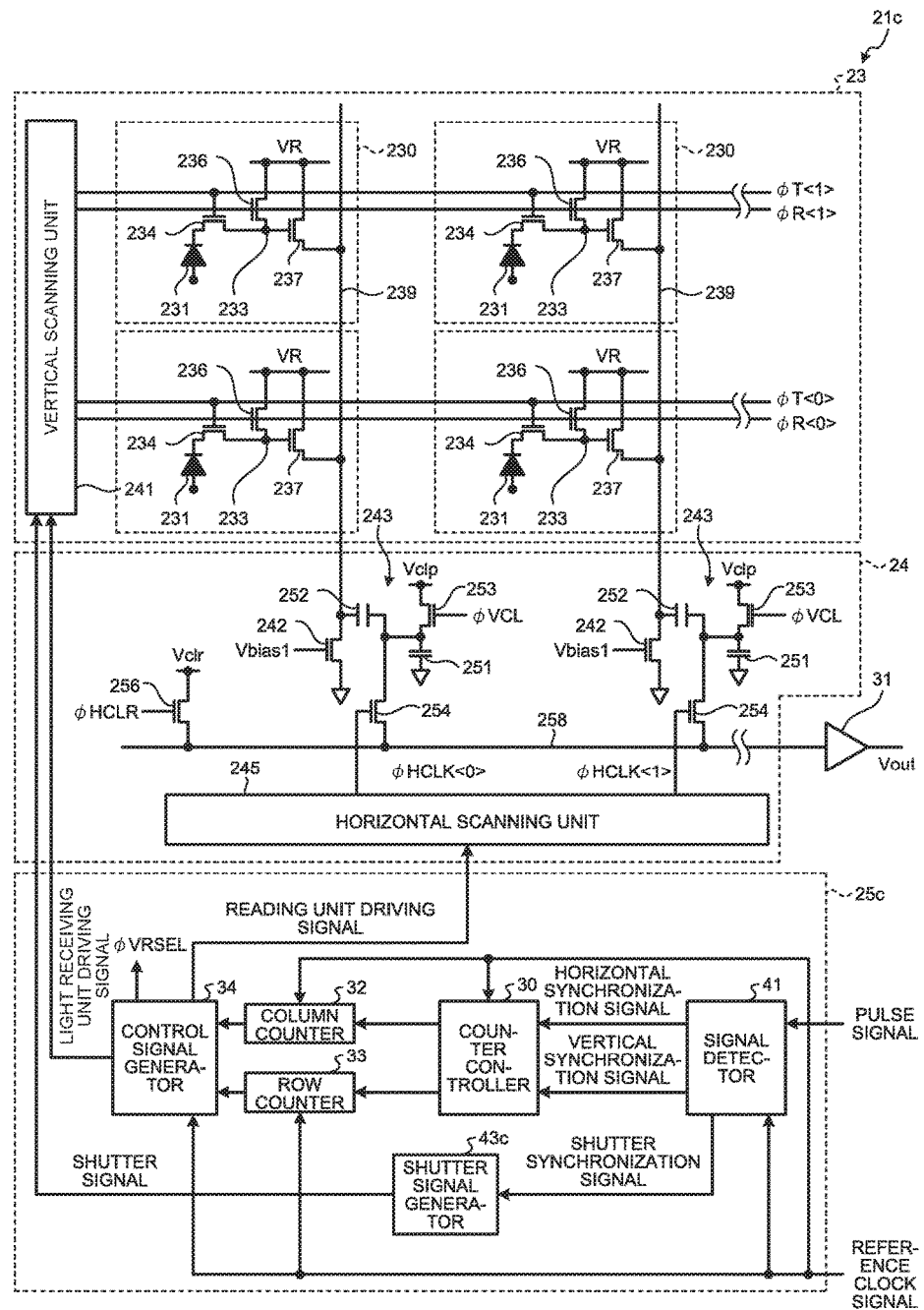
FIG. 12 is a circuit diagram illustrating a configuration of a first chip according to a third embodiment of the disclosure.

FIG. 12 is a circuit diagram illustrating a configuration of a first chip according to the third embodiment of the disclosure. The first chip 21c of FIG. 12 is provided with a timing generator 25c instead of the timing generator 25 of the first chip 21 of the first embodiment described above.

The timing generator 25c generates various driving signals (such as φT, φR, φVCL, φHCLR, φHCLK, and φVRSEL) on the basis of the pulse signal input from the pulse signal detector 27 and the reference clock signal from the connector unit 5, and outputs the driving signals to the vertical scanning unit 241, the noise eliminating unit 243, the horizontal scanning unit 245, and the reference voltage generator 246. In the timing generator 25c, the shutter counter 42 is removed unlike the timing generator 25b of the second embodiment described above.

A shutter signal generator 43c generates the light receiving unit driving signal on the basis of the shutter synchronization signal input from the signal detector 41 and outputs the light receiving unit driving signal to the vertical scanning unit 241, so that the transfer gates of all the unit pixels 230 are reset to perform a global shutter operation.

Detection Operation for Shutter Synchronization Signal Using Timing Generator

Figure 13:
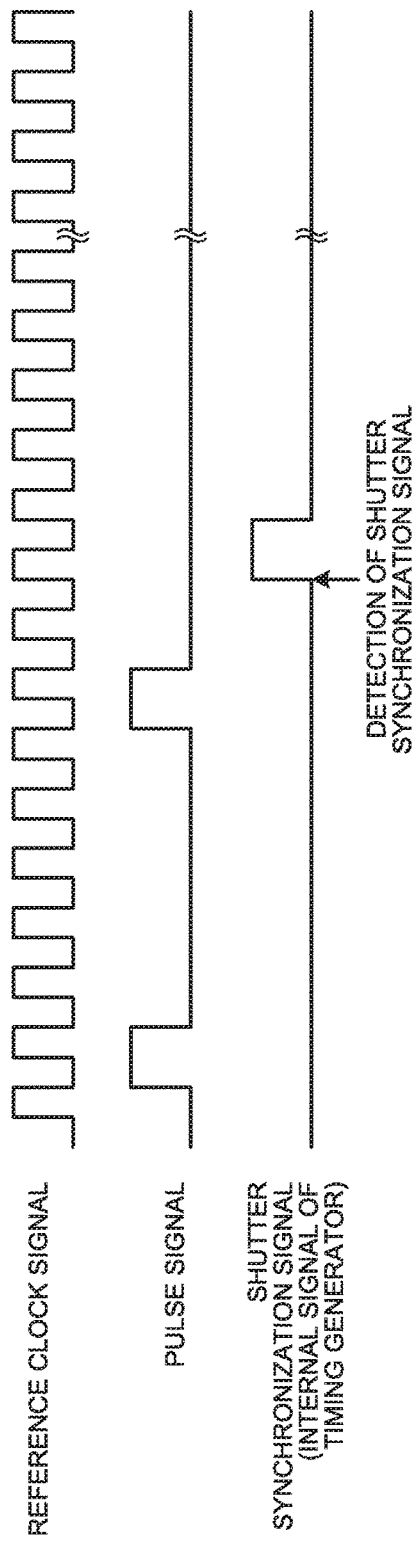
FIG. 13 is a timing chart illustrating operations performed to detect a shutter synchronization signal using a timing generator according to the third embodiment of the disclosure.
Figure 14:
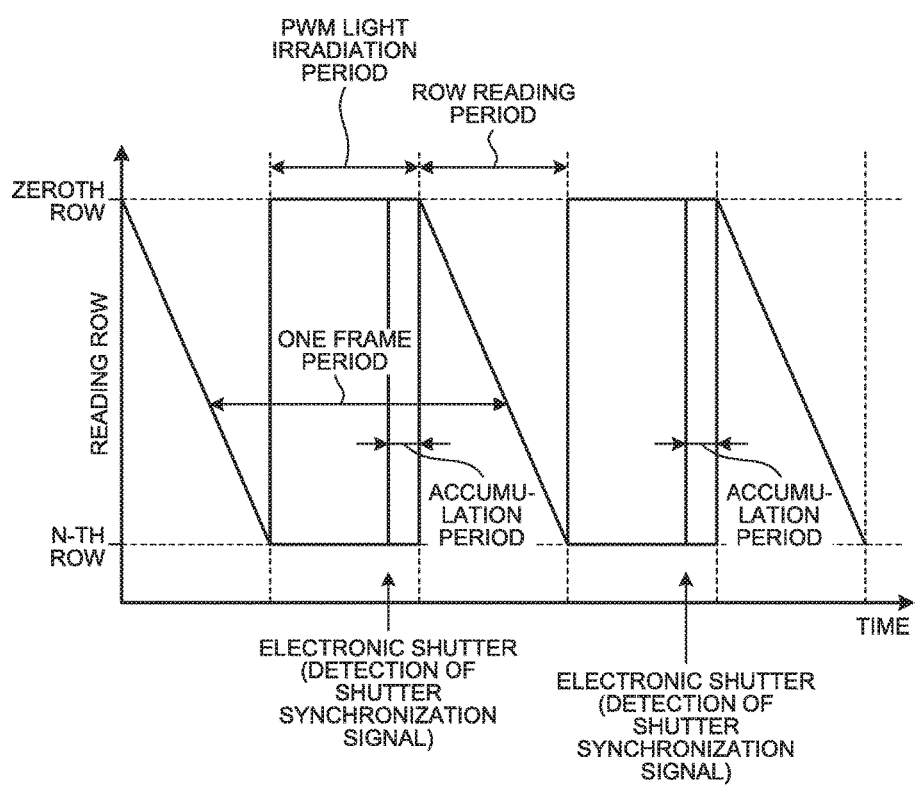
FIG. 14 is a diagram schematically illustrating a timing at which a reading unit reads an imaging signal from each unit pixel of a light receiving unit under control of the timing generator according to the third embodiment of the disclosure.

Next, a detection operation for the shutter synchronization signal using the timing generator 25c will be described. FIG. 13 is a timing chart illustrating operations performed to detect the shutter synchronization signal using the timing generator 25c. FIG. 14 is a diagram schematically illustrating timings at which the reading unit 24 reads the imaging signal from each unit pixel 230 of the light receiving unit 23 under control of the timing generator 25c. In FIG. 13, the reference clock signal, the pulse signal, and the shutter synchronization signal are illustrated in order from the top.

As illustrated in FIG. 13, the signal detector 41 detects the shutter synchronization signal by sampling the pulse signal input from the pulse signal detector 27 using the reference clock signal from the connector unit 5 and decoding the pulse signal.

Subsequently, if the shutter synchronization signal is input from the signal detector 41, the shutter signal generator 43c generates the light receiving unit driving signal and outputs the generated light receiving unit driving signal to the vertical scanning unit 241, so that the transfer gates of all the unit pixels 230 are reset to perform a global shutter operation (refer to FIG. 14).

Then, if the vertical synchronization signal from the signal detector 41 is decoded, the control signal generator 34 resets the row counter 33 and the column counter 32 of the first embodiment described above, so that reading of the imaging signal from the light receiving unit 23 starts.

According to the third embodiment of the disclosure described above, it is possible to reduce the number of the transmission cables 3 while receiving the control signal.

Fourth Embodiment

Next, a fourth embodiment of the disclosure will be described. The endoscope system according to the fourth embodiment is different from the endoscope system of the first embodiment described above in the configuration of the first chip 21. Specifically, the pulse signal superimposed on the negative voltage is expanded, and the light receiving unit 23 is driven by a serial command for any control operation. In the following description, a configuration of the timing generator according to the fourth embodiment will be described. Note that like reference numerals denote like elements as in the endoscope system 1 of the first embodiment described above, and they will not be repeatedly described.

Specific Configuration of First Chip

Figure 15:
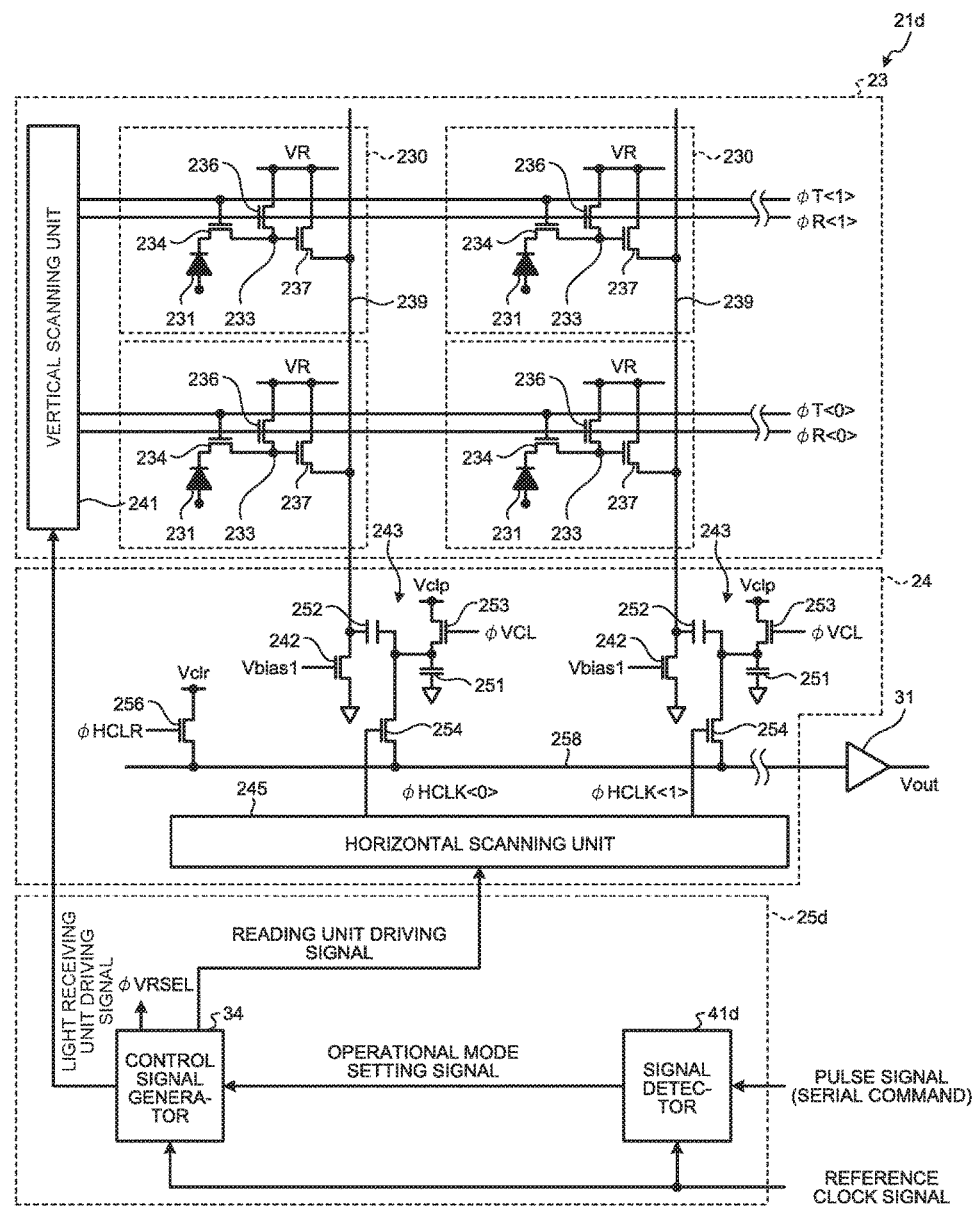
FIG. 15 is a circuit diagram illustrating a configuration of a first chip according to a fourth embodiment of the disclosure.

FIG. 15 is a circuit diagram illustrating a configuration of a first chip according to the fourth embodiment of the disclosure. The first chip 21d of FIG. 15 is provided with a timing generator 25d instead of the timing generator 25 of the first chip 21 of the first embodiment described above.

The timing generator 25d generates various driving signals (such as φT, φR, φVCL, φHCLR, φHCLK, and φVRSEL) on the basis of the pulse signal input from the pulse signal detector 27 and the reference clock signal from the connector unit 5, and outputs the driving signals to the vertical scanning unit 241, the noise eliminating unit 243, the horizontal scanning unit 245, and the reference voltage generator 246. The timing generator 25d has a signal detector 41d and a control signal generator 34.

The signal detector 41d decodes the pulse signal (serial command) input from the pulse signal detector 27 and outputs an operational mode setting signal to the control signal generator 34.

The control signal generator 34 generates various driving signals in response to the operational mode setting signal transmitted from the signal detector 41d to drive the first chip 21d.

According to the fourth embodiment of the disclosure described above, it is possible to reduce the number of the transmission cables 3 while receiving the control signal.

According to the fourth embodiment of the disclosure, by providing the serial command decoder in the signal detector 41d, it is possible to perform any control operation by expanding the pulse signal superimposed on the negative voltage.

According to the disclosure, the separator 26 and the pulse signal detector 27 or 27a may be provided in the second chip 22. Naturally, the chip configuration of the imaging unit 20 or 20a may be appropriately changed in order to implement miniaturization of the distal end portion.

According to some embodiments, it is possible to reduce the number of the I/O terminals while receiving the control signal.

In the description for the timing charts of this disclosure, procedural expressions such as "first," "then," or "subsequently" are used to specify a sequential relationship between each process. However, the processing sequence necessary in the disclosure is not uniquely determined by such expressions. That is, the processing sequence in the timing charts described herein may be changed as long as it is not contradictory.

In this manner, the disclosure encompasses various embodiments although they are not explicitly described herein. In addition, various design changes or the like may be possible without departing from the spirit and scope of the present invention as disclosed in the attached claims.

What is claimed is:

1. An imaging device comprising:
   an image sensor including a plurality of pixels arranged in a two-dimensional matrix shape, each pixel being configured to receive external light and generate an imaging signal depending on an amount of the received light;
   a transmission cable configured to transmit power to the image sensor;
   a power source provided on a proximal end side of the transmission cable and configured to supply a voltage to the image sensor;
   a pulse signal superimposing unit provided on the proximal end side of the transmission cable and configured to superimpose a pulse signal on the voltage;
   a separator connected between the image sensor and the transmission cable and configured to separate an offset voltage and a pulse voltage from the voltage transmitted from the transmission cable and output the offset voltage to the image sensor;
   a pulse signal detector connected between the separator and the transmission cable on a distal end side of the transmission cable and configured to detect the pulse signal superimposed on the offset voltage; and
   a timing generator configured to generate, based on the pulse signal detected by the pulse signal detector, a driving signal for driving the image sensor.

2. The imaging device according to claim 1, wherein the timing generator includes a synchronization signal generator configured to generate, based on the pulse signal detected by the pulse signal detector and a reference clock signal input from outside, a synchronization signal for driving the image sensor as the driving signal.

3. The imaging device according to claim 1, wherein the timing generator includes:
   a signal detector configured to generate a horizontal synchronization signal, a vertical synchronization signal, and a shutter synchronization signal of the image sensor based on the pulse signal detected by the pulse signal detector and a reference clock signal input from outside; and
   a driving signal generator configured to generate the driving signal based on the shutter synchronization signal generated by the signal detector.

4. The imaging device according to claim 1, wherein the timing generator includes:
   a serial command decoder configured to decode, based on the pulse signal detected by the pulse signal detector and a reference clock signal input from outside, a serial command input from outside; and
   a driving signal generator configured to generate, based on a result of the decoding, a driving signal for driving the image sensor.

5. The imaging device according to claim 1, wherein the pixel includes:
   a photoelectric converter;
   a charge-voltage converter;
   an electric charge transfer portion configured to transfer an electric charge from the photoelectric converter to the charge-voltage converter;
   a charge-voltage converter reset unit configured to reset the charge-voltage converter; and
   an output unit configured to output a signal obtained by voltage conversion of the charge-voltage converter,
   wherein the power source is configured to supply the voltage to at least one of the electric charge transfer portion and the charge-voltage converter reset unit through the transmission cable.

6. An endoscope comprising:
   the imaging device according to claim 1;
   an insertion portion insertable into a subject; and
   a connector unit detachably installed in an image processing device configured to perform image processing for the imaging signal,
   wherein the image sensor, the separator, the pulse signal detector, and the timing generator are provided on a distal end side of the insertion portion, and
   the power source and the pulse signal superimposing unit are provided in the connector unit.

7. An endoscope system comprising:
   the endoscope according to claim 6; and
   an image processing device configured to perform image processing for the imaging signal.

* * * * *